United States Patent [19]

Felix et al.

[11] Patent Number: 5,334,787
[45] Date of Patent: Aug. 2, 1994

[54] PROCESS FOR THE MANUFACTURE OF PENTAFLUOROETHANE

[75] Inventors: Vinci M. Felix, Kennett Square, Pa.; William H. Gumprecht, Wilmington, Del.; Barry A. Mahler, Glen Mills, Pa.

[73] Assignee: E. I. Du Pont de Nemours and Company, Wilmington, Del.

[21] Appl. No.: 989,481

[22] Filed: Nov. 12, 1992

Related U.S. Application Data

[63] Continuation of Ser. No. 834,798, Feb. 13, 1992, abandoned, which is a continuation-in-part of Ser. No. 695,900, May 6, 1991.

[51] Int. Cl.$^5$ ............................................. C07C 17/08
[52] U.S. Cl. ..................................................... 570/169
[58] Field of Search ................................. 570/168, 169

[56] References Cited

U.S. PATENT DOCUMENTS

| | | | |
|---|---|---|---|
| 3,258,500 | 6/1966 | Swamer et al. | 260/653.7 |
| 3,755,477 | 8/1973 | Firth et al. | 260/653.4 |
| 4,158,675 | 6/1979 | Potter | 260/653.7 |
| 4,843,181 | 6/1989 | Gumprecht | 570/168 |
| 5,087,329 | 2/1992 | Felix | 203/67 |

FOREIGN PATENT DOCUMENTS

| | | |
|---|---|---|
| 849024 | 8/1970 | Canada . |
| 1124265 | 5/1982 | Canada . |
| 1196345 | 11/1985 | Canada . |
| 0036123 | 9/1981 | European Pat. Off. . |
| 0313061 | 4/1989 | European Pat. Off. . |
| 0349298 | 1/1990 | European Pat. Off. . |
| 0403108 | 12/1990 | European Pat. Off. . |
| 0456552 | 11/1991 | European Pat. Off. . |
| 2806865 | 10/1978 | Fed. Rep. of Germany . |
| WO8911467 | 11/1989 | PCT Int'l Appl. . |
| 901297 | 7/1962 | United Kingdom ................ 570/169 |

*Primary Examiner*—Alan Siegel
*Attorney, Agent, or Firm*—Michael K. Boyer

[57] ABSTRACT

An improved process for the manufacture of $CF_3CHF_2$ by contacting 1,2-dichloro-1,1,2-trifluoroethane ($CClF_2CHClF$) or 1-chloro-1,1,2,2-tetrafluoroethane ($CHF_2CClF_2$) or mixtures of $CF_3CHCl_2$ and $CClF_2CHClF$ or mixtures of $CF_3CHClF$ and $CHF_2CClF_2$ with HF in the presence of a $Cr_2O_3$ catalyst prepared by pyrolysis of ammonium dichromate, the reaction being conducted under controlled conditions whereby the production of $CF_3CHF_2$ is maximized, and the formation of chloropentafluoroethane ($CF_3CClF_2$) and other perhalo derivatives is minimized. The subject hydrogen-containing compound is useful as a blowing agent, propellant, refrigerant, fire extinguishing agent, or sterilant carrier gas.

13 Claims, No Drawings

PROCESS FOR THE MANUFACTURE OF PENTAFLUOROETHANE

CROSS-REFERENCE TO RELATED APPLICATIONS

This is a continuation of application Ser. No. 07/834,798 filed Feb. 13, 1992, now abandoned which is a continuation-in-part of application Ser. No. 695,900, filed on May 6, 1991, in the names of Vinci M. Felix et al., and entitled "Process for the Manufacture of Pentafluoroethane", the disclosure of which is expressly incorporated by reference.

FIELD OF THE INVENTION

An improved process for the manufacture of pentafluoroethane ($CF_3CHF_2$) comprising a gas-phase reaction of 2,2-dichloro-1,1,1-trifluoroethane ($CF_3CHCl_2$) or 1,2-dichloro-1,1,2-trifluoroethane ($CClF_2CHClF$) or 1,1,1,2-tetrafluorochloroethane ($CF_3CHClF$) or 1,1,2,2-tetrafluorochloroethane ($CHF_2CClF_2$) or mixtures of $CF_3CHCl_2$ and $CClF_2CHClF$ or mixtures of $CF_3CHClF$ and $CHF_2CClF_2$ with HF in the presence of a $Cr_2O_3$ catalyst prepared by pyrolysis of ammonium dichromate, the reaction being conducted under controlled conditions whereby the production of $CF_3CHF_2$ is maximized, and the formation of chloropentafluoroethane ($CF_3CClF_2$) and other perhalo derivatives is minimized. The subject hydrogen-containing compound is useful as a blowing agent, propellant, refrigerant, fire extinguishing agent, sterilant carrier gas, or heavy gas for an aerodynamic wind tunnel. It is desirable for its zero ozone depletion potential.

BACKGROUND OF THE INVENTION

U.S. Pat. No. 3,755,477 describes a process for producing fluorinated aliphatic hydrocarbons which comprises fluorinating a halogenated aliphatic hydrocarbon, including tetrachloroethylene and chlorotrifluoroethylene, by reaction in the gas phase with HF in the presence of a steam-treated and calcined chromium oxide catalyst prepared by a multi-step process. Example 23, column 5, shows tetrachloroethylene as a raw material with formation of $CF_3CHCl_2$ (20%), $CF_3CHClF$ (20%), $CF_3CHF_2$ (30%), and $CF_3CClF_2$ (20%) at 10/1 $HF/C_2Cl_4$ mole ratio, 5.4 seconds contact time and 350° C. reaction temperature. Example 25 shows that, with $CF_3CHCl_2$ as starting material at 390° C., $CF_3CHClF$ (21%) and $CF_3CHF_2$ (67%) are produced, but again these desirable hydrogen-containing products are accompanied by perhalogenated $CF_3CClF_2$ (2.5%). The formation of $CF_3CClF_2$, 20% in 24 and 2.5% in 25, is objectionable; not only does it constitute a yield loss of the hydrogen-containing substances, but $CF_3CClF_2$ is extremely close boiling to $CF_3CHF_2$ with the resulting mix being costly to separate.

U.S. Pat. No. 3,258,500 describes a process for the catalytic vapor-phase reaction of HF with halohydrocarbons employing a catalyst that consists essentially of a heat-activated anhydrous chromium (III) oxide which may be supported on alumina. Example 17, column 14, shows that fluorination of tetrachloroethylene with this catalyst at 400° C. produces 35.0% pentafluoroethane, 9.2% 1,2-tetrafluorochloroethane, and 3.5% 2,2-dichloro-1,1,1-trifluoroethane. At 300° C. the product distribution is 38.3% 1,2-tetrafluorochloroethane, 25.4% pentafluoroethane, and 16.0% 2,2-dichloro-1,1,1-trifluoroethane. Example 20, column 19, shows that chlorotrifluoroethylene at 400° C. yields 27% $CF_3CHF_2$. It can be seen that, although the yield of the hydrogen-containing products is high, that of pentafluoroethane does not exceed about 35% even at temperatures as high as 400° C.

U.S. Pat. No. 4,843,181 discloses a gas phase process for the manufacture of $CF_3CHCl_2$ and/or $CF_3CHClF$ by contacting a suitable tetrahaloethylene and/or pentahaloethane with HF in the presence of $Cr_2O_3$ prepared by pyrolysis of $(NH_4)_2Cr_2O_7$, the reaction being conducted under controlled conditions whereby the production of $CF_3CHF_2$ is minimized.

Canadian Patent No. 849,024 also discloses the formation of $CF_3CHF_2$ by reaction of HF with a perhaloethylene, e.g., $C_2Cl_4$, $CCl_2\!=\!CF_2$ and $CClF\!=\!CF_2$, over a hydrous $Cr_2O_3$ as catalyst, but the $CF_3CHF_2$ yields are relatively poor.

Canadian Patent No. 1,196,345 discloses that addition of HF to perfluoroethylene over a chromium oxyfluoride as catalyst, which has been activated by treatment with a mixture of HF and $F_2$, produces $CF_3CHF_2$ in high yields. Much inferior yields are obtained using a comparable catalyst activated with HF alone. The disclosed process suffers in that the catalyst activation step not only involves the use of expensive and hazardous molecular fluorine, but requires a back-up scrubbing solution of hexafluoropropylene trimer to scavenge unreacted $F_2$. All this represents a loss of $F_2$ and catalyst activation potential, and further adds to the cost of the process.

The prior art, in general, has shown that $CF_3CHCl_2$ is obtainable in good yields from tetrachloroethylene, a readily available and relatively inexpensive commodity. However, $CF_3CHCl_2$ as starting material for the production of highly fluorinated hydrogen-containing products by reaction with HF also yields perhalo by-products, evidently via chlorination side reactions, especially when an attempt is made to increase conversion to the desired hydrogen-containing products by operating at high temperatures.

SUMMARY OF THE INVENTION

A process for the preparation of pentafluoroethane which comprises contacting HF with at least one member of the group of $CF_3CHCl_2$, $CClF_2CHClF$, $CF_3CHClF$, $CHF_2CClF_2$, mixtures of $CF_3CHCl_2$ and $CClF_2CHClF$, mixtures of $CF_3CHClF$ and $CHF_2CClF_2$, among others, in the gas phase in the presence of a $Cr_2O_3$ catalyst at a reactant mole ratio, a feed rate of reactant per weight catalyst, temperature and pressure and for a time effective to form a gas product stream containing $CF_3CHF_2$ as the predominant component, the catalyst being prepared by pyrolysis of $(NH_4)_2Cr_2O_7$.

Preferably, the $Cr_2O_3$ catalyst has an alkali metal content of not more than 100 ppm.

Preferably, too, the starting material is $CF_3CHCl_2$, and said conditions are controlled such that the $CF_3CHF_2$ product is substantially free of $CF_3CClF_2$.

This invention is based on the discovery that $Cr_2O_3$ prepared by pyrolysis of $(NH_4)_2Cr_2O_7$ is effective to catalyze conversion of $CF_3CHCl_2$ and the next higher fluorinated intermediate, $CF_3CHClF$, to $CF_3CHF_2$ in high yields at high conversions of the starting materials without undue formation of $CF_3CClF_2$ and other perhalogenated by-products.

Accordingly, it is an object of this invention to provide a process for the production of $CF_3CHF_2$ using $CF_3CHCl_2$ as starting material, which results in the formation of $CF_3CHF_2$ in high yields at high conversions.

Another object of this invention is to provide such process which substantially avoids the formation of close boiling $CF_3CClF_2$.

Still another object of this invention is to provide such process as above that utilizes a catalyst that is readily available and is effective in catalyzing the halogen exchange reaction of HF with a reactant comprising at least one member from the group consisting of $CF_3CHCl_2$ or $CClF_2CHClF$ or $CF_3CHClF$ $CHF_2CClF_2$ or mixtures of $CF_3CHCl_2$ and $CClF_2CHClF$ or mixtures of $CF_3CHClF$ and $CHF_2CClF_2$, among others, such that the formation of $CF_3CHF_2$ is maximized.

DETAILS OF THE INVENTION

The $Cr_2O_3$ catalyst of this invention is prepared by pyrolysis of ammonium dichromate by any method known to the art, including methods such as that described in U.S. Pat. No. 4,471,985 which is incorporated herein by reference.

By pyrolysis is meant heating ammonium dichromate to a sufficient temperature and for a sufficient time to cause the following reaction to occur to substantial completion:

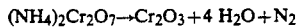

$$(NH_4)_2Cr_2O_7 \rightarrow Cr_2O_3 + 4 H_2O + N_2$$

For example, ammonium dichromate may be heated in a continuous kiln at 500°–700° C., preferably 540°–640° C., for 5–20 minutes so that it will undergo an internal oxidation-reduction reaction to produce mainly water, nitrogen and $Cr_2O_3$. After the water and nitrogen are driven off, the remaining fine powder of $Cr_2O_3$ may be cooled and compacted so as to increase its bulk density for ease of handling. For example, a bulk density of approximately 400–1440 Kg/m³ may be desirable, and typically 448–512 kg/m³.

The $Cr_2O_3$ obtained may contain low levels of contaminants which are present as a result of the manufacturing process for the original $(NH_4)_2Cr_2O_7$. Although not totally destructive of catalyst efficacy, potassium, for example, as a contaminant has an adverse effect on the activity and life of the catalyst of this invention. It is desirable for the amount of potassium and other alkali metals to be 100 ppm by weight or less. The level may be reduced by a water-washing step. While the conditions are not critical, the water-washing step can include forming a slurry containing 5–15% $Cr_2O_3$, preferably 10%, and deionized water. Stirring of this water slurry can be carried out at 35°–65° C. for at least one hour, preferably two or more hours. The solids are then recovered by filtration, suitably on a plate and frame filter press. The filter cake can be analyzed for alkali metal content. If its level is 100 ppm by weight or less (dry basis), the solids are, thereafter, dried. If not, the washing step can be repeated to obtain a desired level of alkali metal content.

The form of the catalyst is not critical and may be used as pellets, powders or granules.

For example, if the catalyst is desired to be in the pellet form, 5–15%, preferably 10%, of chromium acetate and 1–5%, preferably 2% of graphite can be added to the dried solids as pelletization aids. The chromium acetate can be added in aqueous solution of 30–70%, preferably 50% concentration. The resultant paste can be mulled to mix the ingredients and then pelletized to the desired size, preferably 0.32 cm×0.32 cm cylinders. The pellets can be dried at 80°–120° C., preferably 105° C., for 8–48 hours, preferably 16–24 hours. The $Cr_2O_3$ pellets then have a bulk density of 1120–1440 Kg/m³ for the preferred pellet size and a surface area of 40–57 m²/g, preferably 45–55 m²/g. Pore volume is 0.15–0.33 cc/g. The alkali metal content is 100 ppm or less.

Generally, the resulting $Cr_2O_3$ will be pretreated with HF. It is thought that this converts some of the surface chrome oxide to chrome oxyfluoride. This pretreatment can be accomplished by placing the $Cr_2O_3$ in a suitable container, which can be the reactor to be used to perform the reaction of the instant invention, and thereafter, passing HF over the pyrolyzed and dried $Cr_2O_3$ so as to partially saturate the $Cr_2O_3$ with HF. This is conveniently carried out by passing HF over the $Cr_2O_3$ for a period of time, for example, about 15 to 300 minutes at a temperature of, for example, about 200° C. to about 450° C. The purpose of this pretreatment is to prevent damage to the catalyst due to possible high temperature excursions and resultant coking of the catalyst if the organic reactants were contacted with the catalyst without first having conditioned some of the surface chrome oxide with HF. Nevertheless, this pretreatment is not essential; initial process conditions and equipment could be selected so as to avoid the problem of high temperature and coking of the catalyst.

The contacting of the reactants with HF in the presence of the catalyst, preferably pretreated, of the instant invention is performed at effective temperature, mole ratio and contact time. By effective temperature, mole ratio and contact time is meant the temperatures, mole ratios and contact times which produce a product stream which contains $CF_3CHF_2$ in a major proportion, preferably in an amount of at least about 50%, more preferably at least about 60%, as determined by gas chromatography.

When employing a reactant comprising at least one member of the group consisting of $CF_3CHCl_2$, $CClF_2CHClF$, $CF_3CHClF$, $CHF_2CClF_2$, mixtures of $CF_3CHCl_2$ and $CClF_2CHClF$, mixtures of $CF_3CHClF$ and $CHF_2CClF_2$, among others, the temperature will normally range from about 300° to about 370° C., preferably about 330° to 350° C. The $HF/CF_3CHCl_2$ mole ratio will normally range from 2/1 to about 10/1, preferably from about 3/1 to 8/1. The contact time can vary widely but preferably will be such as to provide an average residence time of from about 10 to 100 seconds, more preferably 20 to 50 seconds.

The pressure is not critical but should be sufficient to maintain HF, the organic reactant and the reaction product stream components in the vapor state at the operating temperature.

In general, the higher the temperature, the greater the HF/reactant mole ratio, and the longer the contact time, the greater is the conversion of the reactants to fluorinated products, and the greater is the degree of fluorination of the raw material. The above variables can be balanced, one against the other, so that formation of $CF_3CHF_2$ is maximized and that of perhalogenated by-products is minimized, preferably to less than about 3%, with that of $CF_3CClF_2$ to less than 2%, more preferably to less than 1%, said percents being mole percents as determined by gas chromatography.

Unreacted starting material and intermediate compound(s) can be recycled to the reactor for the production of additional $CF_3CHF_2$. In some cases, the product stream from the reactor may include one or more intermediates compounds such as $CClF_2CHClF$, $CF_3CHCl_2$, $CF_3CHFCl$, $CHF_2CClF_2$, among others, which can be recycled to the reactor in order to increase the yield of $CF_3CHF_2$. Without wishing to be bound by any particular theory or explanation, it is believed that employing one or more of the $CF_3CHF_2$ intermediate compounds as a reactant may increase the rate at which $CF_3CHF_2$ is produced. For example, at least a portion of the starting materials or reactants, which are introduced into the reactor, can comprise at least one intermediate compound(s), that are either virgin and/or obtained as recycled components.

The reaction of the reactants with HF may be conducted in any suitable reactor, included fixed and fluidized bed reactors. The reaction vessel should be constructed from materials which are resistant to the corrosive effects of hydrogen fluoride and hydrogen chloride, such as "Hastelloy" and "Inconel".

EXAMPLES

The catalyst used in the following runs was $Cr_2O_3$ prepared by pyrolyzing $(NH_4)_2Cr_2O_7$ as described above and had an alkali metal content of 60 ppm. It was in cylindrical pellet form, ⅛ inch long (3.2 mm) and ⅛ inch (3.2 mm) in diameter; its bulk density was about 100 lbs/cubic foot (1602 $Kg/m^3$). The catalyst was packed in a Schedule 40 "Inconel" 600 U-shaped pipe reactor, 1 inch (25.4 mm) in diameter and 4 feet long (1.2 m), which was immersed in a temperature-controlled molten salt bath which provided isothermal reaction conditions.

The catalyst was activated by gradually heating the packed reactor to 400° C. while $N_2$ gas at a flow rate of 50 ml/minute was passed through it to remove trace water. The temperature was lowered to 200° C., and HF and $N_2$ gases (1:4 molar ratio) were passed through the reactor. The HF employed for activation and all of the $CF_3CHF_2$ production runs was commercial grade containing only trace amounts of water. The $N_2$ flow was decreased with time until neat HF was passing through the reactor. At this point, the temperature was gradually raised to 420° C. and maintained for 16 hours.

For hydrofluorination, the reactor temperature was decreased to that indicated in the runs described below. The organic and HF feeds were vaporized external to the salt bath, mixed and fed to a separate catalyst-free section of the pipe reactor, which served as a preheater, before entering the catalyst-packed reactor. The reactant flows were adjusted to give the indicated rates, mole ratios and average residence times, calculated by dividing the volume of the reactor by the volumetric flow rate of the combined HF and organic feeds at the temperature and pressure of operation. The reaction temperature was determined by the salt bath temperature; the pressure was set by a back-pressure regulator.

The reactor effluent was scrubbed with aqueous KOH, and its composition determined with an in-line gas chromatograph. The chromatograph was equipped with a flame ionization detector and used a 20 foot (6.1 m) long, ⅛ inch (3.2 mm) diameter column, packed with "Krytox" perfluorinated polyether on an inert support, and a helium carrier at a flow rate of 20 cc/minute. The gas chromato-graph was temperature programmed such that it was held at 40° C. for 4 minutes, followed by a temperature ramp of 5°/minute until 180° C. was reached and maintained for 5 minutes. The results recorded below are in mole percent.

EXAMPLE 1

A mixture of HF and $CF_3CHCl_2$ was fed to the reactor at a mole ratio of $HF/CF_3CH_2Cl_2 = 6:1$ and a $CF_3CHCl_2$ feed rate of 0.333 m/hour (0.151 Kg/hour) per pound of catalyst. The reaction pressure was 100 psig (7.8 atmospheres); the temperature was varied in a series of runs as tabulated in Table 1.

TABLE 1

| Run | Temp. °C. | $CF_3CHF_2$ | $CF_3CHClF$ | $CF_3CHCl_2$ | $CF_3CClF_2$ | Other* |
|---|---|---|---|---|---|---|
| 1 | 305 | 6.6 | 52.1 | 40.9 | 0.0 | 0.4 |
| 2 | 315 | 14.9 | 57.0 | 27.6 | 0.0 | 0.5 |
| 3 | 325 | 36.4 | 44.0 | 18.8 | 0.04 | 0.8 |
| 4 | 340 | 67.5 | 19.3 | 11.2 | 0.22 | 1.8 |

*Included $CF_3CH_2F$, $CClF_2CHF_2$, $CF_3CH_2Cl$, $CF_3Cl_2F$, $CClF_2CClF_2$ and $CClF_2CHClF$, each in an amount of less than 1%.

The results show that the invention catalyst is highly effective to catalyze the conversion of $CF_3CHCl_2$ to hydrogen-containing products at relatively moderate temperatures, and that the $CF_3CHF_2$ make increases sharply with increasing $CF_3CHCl_2$ conversions at increasing temperatures without undue production of perhalo by-products.

Lowering the $CF_3CHCl_2$ feed rate results in its increased conversion to $CF_3CHClF$ and subsequently to $CF_3CHF_2$. This is illustrated in the following Examples.

EXAMPLE 2

The procedure of Example 1 was repeated except that the temperature was held constant at about 326° C. The $HF/CF_3CHCl_2$ mole ratio (MR), the $CF_3CHCl_2$ feed rate (FR) and the average residence time (ART) in seconds are tabulated in Table 2.

TABLE 2

| Run | MR | FR | $CF_3CHF_2$ | $CF_3CHClF$ | $CF_3CHCl_2$ | Other* | ART |
|---|---|---|---|---|---|---|---|
| 1 | 6/1 | 0.333 | 40.7 | 42.1 | 16.4 | 0.8 | 30 |
| 2 | 5.4/1 | 0.3 | 44.6 | 42.4 | 12.5 | 0.5 | 29 |
| 3 | 5.6/1 | 0.222 | 56.2 | 30.6 | 12.1 | 1.1 | 48 |
| 4 | 10/1 | 0.111 | 63.6 | 26.2 | 7.0 | 3.2 | 60 |
| 19 | 7/1 | 0.111 | 70.8 | 19.8 | 6.9 | 2.5 | 73 |

*Included were $CF_3CH_2F$, $CClF_2CHF_2$, $CF_3CH_2Cl$, $CClF_2CHClF$, $CCl_2FCHClF$, $CF_3CCl_3$ and $CF_3CClF_2$, each in an amount less than 1%.

It will be noted that conversion of $CF_3CHCl_2$ to $CF_3CHF_2$ is high, even at a temperature as low a 326° C., and the conversion increases with decreasing $CF_3CHCl_2$ feed rate per unit weight of catalyst.

EXAMPLE 3

Example 2 was repeated except the temperature was 350°-351° C., and the mole ratios were varied, as noted in Table 3.

TABLE 3

| Run | MR | FR | $CF_3CHF_2$ | $CF_3CHClF$ | $CF_3CHCl_2$ | Other* | ART |
|---|---|---|---|---|---|---|---|
| 1 | 5.2/1 | 0.333 | 79.1 | 11.5 | 6.9 | 2.5 | 32 |
| 2 | 5.1/1 | 0.333 | 75.6 | 13.8 | 8.2 | 2.4 | 29 |
| 3 | 6/1 | 0.222 | 81.9 | 10.3 | 5.2 | 2.6 | 43.5 |
| 4 | 5.8/1 | 0.222 | 80.2 | 11.0 | 6.0 | 2.8 | 42.5 |
| 5 | 8/1 | 0.111 | 85.9 | 7.9 | 3.2 | 3.0 | 66 |

*Included were $CF_3CH_2F$, $CClF_2CHF_2$, $CF_3CH_2Cl$, $CClF_2CHClF$, $CF_3CCl_3$, $CClF_2CClF_2$, $CF_3CCl_2F$, $CClF_2CCl_2F$ and $CF_3CClF_2$, with the $CF_3CClF_2$ make reaching a maximum of about 1% in Run 5. No other by-product amounted to more than 1%.

Again, the results demonstrate the outstanding activity of the subject catalyst to promote the production of $CF_3CHF_2$ at the expense of chlorine-containing perhalo side-products, even at 350° C. The overall results show that, the higher the temperature and the greater the residence time, the higher the conversion and the yields, with the yields of hydrogen-containing products amounting to 90% or better in Runs 3, 4 and 5. This is particularly significant since an effective quantity of at least one of the intermediate compounds such as $CF_3CHClF$, $CHF_2CClF_2$, among others, e.g., listed as "Other" in the above Tables 1-3, can be recycled for further production of the desired pentafluorinated ethane, e.g., the yield of pentafluoroethane is increased. In other words, the intermediate compounds can be reacted individually, or admixed with other intermediate compounds and/or reactants for producing pentafluoroethane.

We claim:

1. A process for the preparation of $CF_3CHF_2$ comprising:
   (a) contacting HF with at least one reactant comprising a material selected from the group consisting of $CF_3CHCl_2$, $CClF_2CHClF$, $CF_3CHClF$, and $CHF_2CClF_2$, in the gas phase in the presence of a solid $Cr_2O_3$ catalyst at a temperature of about 300° to 370° C. and an HF/reactant mole ratio of about 2/1 to 10/1 for a time of about 10 to 100 seconds to form a product stream comprising at least about 50 mole % $CF_3CHF_2$, and less than about 2 mole % $CF_3CClF_2$; and thereafter,
   (b) separating and recovering $CF_3CHF_2$ from the product stream.

2. The process of claim 1 wherein the temperature is 330° to 350° C.

3. The process of claim 2 wherein the $CF_3CHF_2$ content is at least about 60 mole % of the gas product stream as determined gas-chromatographically.

4. The process of claim 1 wherein said material comprises a mixture of $CF_3CHCl_2$ and $CClF_2CHClF$.

5. The process of claim 1 wherein said material comprises a mixture of $CF_3CHClF$ and $CHF_2CClF_2$.

6. A process for producing pentafluoroethane comprising the steps of:
   (a) contacting hydrogen fluoride with a material comprising at least one member selected from the group consisting of $CClF_2CHClF$ and $CHF_2CClF_2$, in the presence of chrome oxide at a temperature of about 300° to 370° C., and an HF/reactant mole ratio of about 2/1 to 10/1 for a time of about 10 to 100 seconds wherein at least a portion of said at least one member is converted to a product stream comprising at least about 50 mole % pentafluoroethane and less than about 2 mole % perhalogenated by-products and;
   (b) recovering the pentafluoroethane.

7. The process of claim 6 wherein said chrome oxide has an alkali metal content of less than about 100 ppm.

8. The process of claim 6 further comprising pretreating said chrome oxide with hydrogen fluoride before said contacting.

9. The process of claim 6 further comprising recycling at least a portion of said at least one member.

10. A process for increasing the yield of pentafluoroethane comprising the steps of:
    (a) contacting hydrogen fluoride with a reactant comprising at least one member of the group consisting of $CF_3CHCl_2$, and $CF_3CHClF$, in the presence of chrome oxide,
    (b) introducing a quantity of a compound comprising at least one member of the group consisting of $CClF_2CHClF$, and $CHF_2CClF_2$, wherein at least a portion of said reactant and said compound is converted to a pentafluoroethane, wherein the temperature ranges from about 300° to 370° C. and the HF/reactant mole ratio ranges from about 2/1 to 10/1 for a time of about 10 to 100 seconds and the quantity of said compound is sufficient to increase the yield of pentafluoroethane,
    (c) producing a product stream comprising at least 50 mole % pentafluoroethane and less than 2 mole % perhalogenated by-products, and
    (d) recovering the pentafluoroethane.

11. The process of claim 1 wherein said chrome oxide is prepared by pyrolysis of ammonium dichromate.

12. The process of claim 6 wherein said chrome oxide is prepared by pyrolysis of ammonium dichromate.

13. The process of claim 10 wherein said chrome oxide is prepared by pyrolysis of ammonium dichromate.

* * * * *